(12) United States Patent
Adams et al.

(10) Patent No.: US 6,290,657 B1
(45) Date of Patent: Sep. 18, 2001

(54) PRENATAL UTERINE MONITORING AND TRENDING SYSTEM

(75) Inventors: John M. Adams, Issaquah; David G. Reuter, Bothell, both of WA (US)

(73) Assignee: Reproductive Health Technologies, Inc., Galveston, TX (US)

( * ) Notice: Subject to any disclaimer, the term of this patent is extended or adjusted under 35 U.S.C. 154(b) by 0 days.

(21) Appl. No.: 09/212,777

(22) Filed: Dec. 16, 1998

(51) Int. Cl.[7] ........................................... A61B 5/11
(52) U.S. Cl. ................................................ 600/591
(58) Field of Search ........................ 600/546, 591; 128/904

(56) References Cited

U.S. PATENT DOCUMENTS

| | | | |
|---|---|---|---|
| 4,738,268 | * 4/1988 | Kipnis | 128/775 |
| 5,301,680 | * 4/1994 | Rosenberg | 128/733 |
| 5,400,799 | * 3/1995 | Yoches et al. | 128/778 |
| 5,581,369 | * 12/1996 | Righter et al. | 358/442 |
| 5,791,342 | * 8/1998 | Woodward | 128/630 |

* cited by examiner

*Primary Examiner*—William E. Kamm
(74) *Attorney, Agent, or Firm*—Locke, Liddell & Sapp LLP

(57) ABSTRACT

There is disclosed a system for monitoring a prenatal condition of a patient and reporting the monitored condition. The system includes a monitor which may be worn by the patient and which generates an electrical signal representing uterine electrical activity of the patient. A microprocessor is configured for analyzing a characteristic of the electrical signal to generate data indicative of the condition and a transmitter transmits the generated data to a receiver, separated from the monitor. The receiver receives the transmitted data and includes a display for displaying the received data.

28 Claims, 2 Drawing Sheets

PRENATAL UTERINE MONITORING AND TRENDING SYSTEM

BACKGROUND OF THE INVENTION

The present invention is generally directed to a system and method for providing long-term monitoring of uterine activity of an animal. The present invention is more particularly directed to such a system and method wherein a monitor is wearable by a patient and provides long-term monitoring and trending of uterine activity during the prenatal period of a human.

Prolonged pregnancy, generally classified as a gestational age exceeding 42 weeks of gestation, is associated with increased perinatal morbidity and mortality. Specifically, in addition to the increased neonatal deaths, there is an increase in the meconium aspiration, depressed infant at five minutes, and cesarean section rate. The mortality from meconium aspiration can be as high as 38% for those women managed expectantly.

Preterm delivery, or delivery before 37 weeks of gestation, occurs in over 10% of births and also contributes directly to neonatal morbidity and mortality. For infants born between 25 and 30 weeks gestation, the mortality rates are between 10% and 20%. The morbidity of the surviving infants correlates directly with the degree of prematurity. Common problems for the infant include respiratory distress syndrome (RDS) which may require chronic oxygen therapy, intra-ventricular hemorrhage (IVH) which is a harbinger of cerebral palsy, necrotizing enterocolitis (NEC) which can lead to short gut and chronic malnutrition, and patent ductus arteriosus (PDA) which contributes to pulmonary edema and respiratory distress. The incidence of these complications for infants born at 28 and 32 weeks gestation are summarized in Table I below.

TABLE I

|     | 28 Weeks | 32 Weeks |
| --- | -------- | -------- |
| RDS | 64%      | 28%      |
| IVH | 4%       | 1%       |
| NEC | 25%      | 6%       |
| PDA | 43%      | 9%       |

The incidence of neonatal morbidity can be significantly reduced if a woman with premature labor receives corticosteroid therapy for one to two days prior to delivery. For example, antenatal glucocorticoid treatment decreases the incidence of RDS, with an odds ratio of 0.31. The incidence of pariventricular hemorrhage and NEC are reduced as well. Clearly, premature labor leading to preterm delivery contributes greatly to neonatal morbidity and mortality, and efforts to delay delivery frequently result in an improved neonatal outcome.

Electrical energy applied to the myometrium or uterine muscle has been proposed to inhibit or initiate uterine contractions. One system and method to this end is disclosed in Karsdon, U.S. Pat. Nos. 5,447,526 and 5,713,940 which are incorporated herein by reference. In accordance with a preferred embodiment disclosed in these patents, a first or positive electrode is placed in surface contact to a woman's abdomen over the top of the uterus. Four negative electrodes are placed in spaced apart relation in surface contact to the woman's abdomen over lower portions of the uterus beginning at approximately a mid portion of the uterus. The negative electrodes and the positive electrode are then connected to a muscle controller which generates square wave pulse trains of current between the positive electrode and the negative electrodes. The muscle controller is capable of providing current pulse trains of selectable polarity. The controller is activated to inhibit uterine contractions when they are undesirably present or to initiate uterine contractions when they are undesirably absent.

In accordance with a further embodiment disclosed in the above-referenced Karsdon patents, a uterine contraction monitor is added to the system with feedback to the controller. The amount of electrical energy applied is thus responsive to the sensed contractions. The feedback may be negative or positive depending upon whether contraction initiation or inhibition is desired.

The application of electrical energy to the myometrium as taught in the Karsdon patents is believed to hold great promise in the management of premature labor and prolonged term pregnancies. However, neither of the Karsdon patents addresses the issue of the long-term monitoring of such patients to facilitate a prediction of whether premature labor inhibition or prolonged term pregnancy labor initiation may be required for a patient.

SUMMARY OF THE INVENTION

The invention therefore provides a monitor for monitoring a prenatal condition of a patient and reporting the monitored conditions. The system includes a monitor adapted to be coupled to the patient including means for generating an electrical signal representing uterine electrical activity of the patient, analyzing means for analyzing a characteristic of the electrical signal to generate data indicative of the condition, and a transmitter for transmitting the generated data. The system further includes a receiver, separated from the monitor, for receiving the transmitted data and including a display for displaying the received data.

The invention further provides a monitor for monitoring a prenatal condition of a patient and reporting the monitored condition. The monitor includes electrical signal generating means for generating an electrical signal representing uterine electrical activity of the patient, analyzing means for analyzing a characteristic of the electrical signal to generate data indicative of the condition, and a transmitter for transmitting the generated data to a separate receiver for display.

The invention still further provides a monitor for monitoring a prenatal condition of a patient including electrical signal means for generating an electrical signal representing uterine electrical activity of the patient, analyzing means for analyzing a characteristic of the electrical signal to generate data indicative of the condition, and alarm means for providing a perceptible indication when the generated data satisfies predetermined criteria.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference numerals identify identical elements, and wherein:

DETAILED DESCRIPTION

Figure 1:
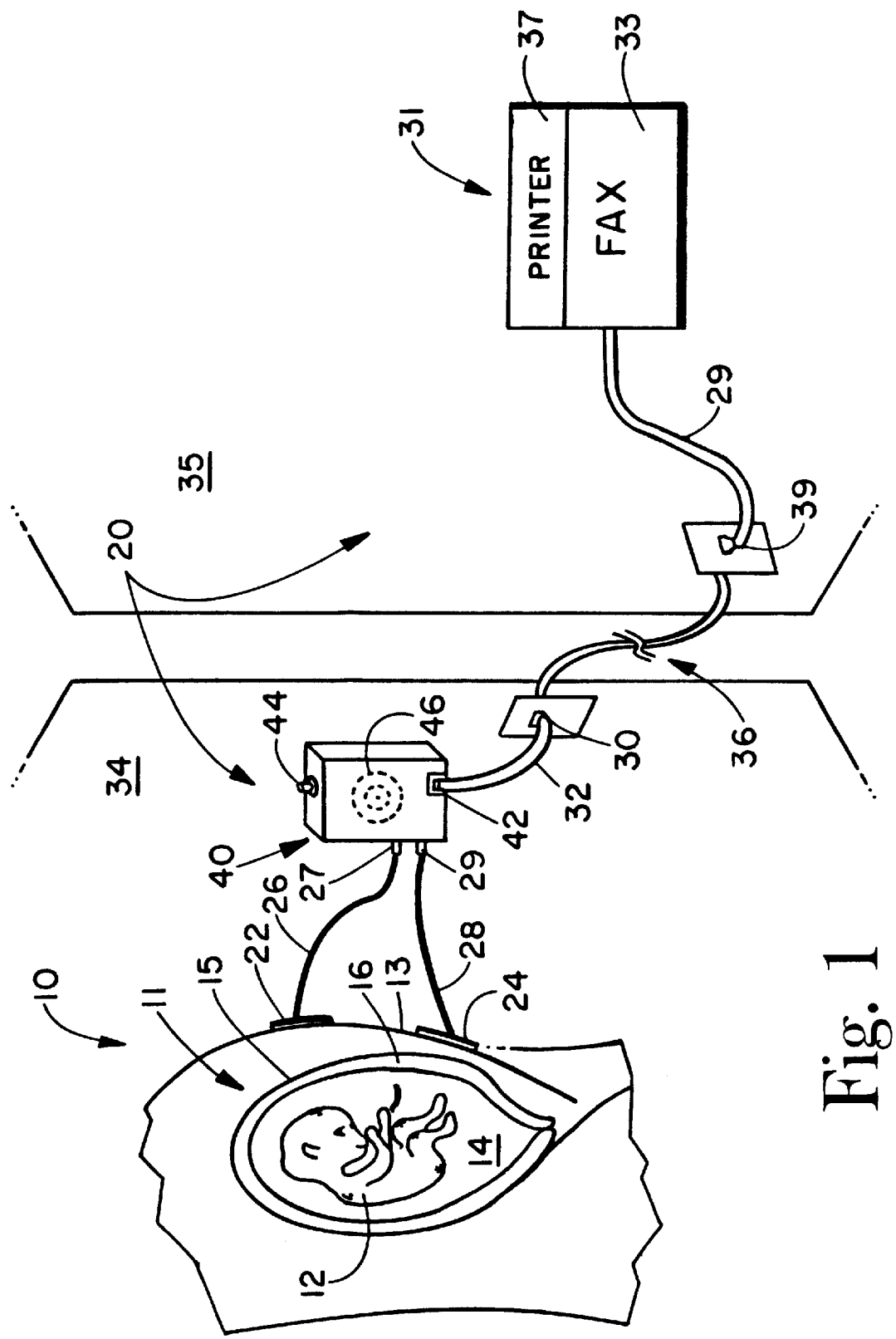
FIG. 1 is a schematic representation of a prenatal uterine monitoring system for providing long-term prenatal uterine monitoring and trending in accordance with a preferred embodiment of the present invention.

Referring now to FIG. 1, it schematically illustrates a monitoring system 20 for providing long-term prenatal uterine monitoring of a partially depicted pregnant patient 10. As will be noted in the figure, the patient has a uterus 11 and a fetus 12 disposed within the uterus 11. The uterus is enclosed by the abdominal wall 13 of the patient and includes an amniotic cavity 14 which is defined by the uterine wall 15. The uterine wall 15 is primarily comprised of the uterine muscle or myometrium 16. As is well known, the fetus 12 is disposed within amniotic fluid contained within the amniotic cavity 14.

The electrical activity of the uterus can exhibit two distinct forms of activity. One form is that of a uterine contracture which is exhibited long before actual labor. Contractures are represented by bursts of electrical activity which can last on the order of several minutes per burst and which are widely spaced apart by separations of an hour or more. Contractures are disorganized muscle activity of the myometrium causing minimal, if any, physical manifestations of the myometrium.

The other form is that of a uterine contraction.

Contractions are represented by relatively short bursts of electrical energy with the bursts being relatively closely spaced apart. For example, uterine contraction electrical bursts of energy may have durations ranging from, for example, several seconds per bursts with separations on the order of minutes. Contractions, as compared to contractures, are organized muscle activity of the myometrium causing pronounced physical manifestations of the myometrium. It is the occurrence of contractions that is most identified as labor.

In accordance with the present invention, the condition of the uterus is monitored long term by ascertaining the durations of uterine electrical bursts and the intraburst separations or burst frequency intervals. At the end of data acquisition periods, for example, at six-hour intervals or four times per twenty-four hour period, the durations and burst frequency intervals for the uterine muscle electrical bursts occurring during the last data acquisition period are averaged. The average burst duration and average burst frequency interval, along with a corresponding time stamp, are then stored for later retrieval. This provides a trend, over time, of the condition of the patient's uterus. Once retrieved, this data can be very valuable to the physician in evaluating the condition of the patient. For example, it is generally known that normal patients not likely to have premature labor exhibit increased uterine electrical activity at night. The uterine activity burst frequency intervals of these patients are generally less during the day than at night. Conversely, patients likely to have premature labor generally do not exhibit increased uterine activity at night. Hence, for these patients, the uterine activity burst frequency intervals tend to be about the same during the day and at night. As a result, by time stamping the average burst frequency interval every six hours, the physician is provided with a diurnal pattern of uterine activity to assist in predicting potential premature labor.

Other features and advantages of the present invention will become apparent as attention is once again directed to FIG. 1. The monitoring system 20 includes a monitor 40 which is coupled to the patient 10 by electrodes 22 and 24 and leads 26 and 28 respectively. The monitor 40 is dimensioned so as to be readily worn by the patient 10. The electrodes 22 and 24 as illustrated are surface electrodes of the type well known in the art which make electrical contact with the patient's abdomen 13. The leads 26 and 28 are electrically coupled to the electrodes 22 and 24 respectively. As is also well known in the art, the leads 26 and 28 may be detachable from the electrodes 22 and 24 respectively when activity of the patient so dictates.

The leads 26 and 28 include connectors 27 and 29 respectively for connection to the monitor 40. When the electrodes 22 and 24 are coupled to the patient and when the leads 26 and 28 are coupled between the electrodes 22 and 24 respectively and the monitor 40, internal circuitry of the monitor to be described subsequently generates an electromyographic signal (EMG) representing the electrical activity of the uterus 11.

The internal circuitry within the monitor as described subsequently analyzes the EMG signal whenever there is a burst of electrical activity of the myometrium 16. For each such burst, a microprocessor within the monitor 40 determines the duration of the burst and the time span or interval between the starting time of the present or most recent burst and the starting time of the immediately preceding burst. The microprocessor then stores these acquired data or results in a memory. At the end of a data acquisition period, for example, six hours, the microprocessor accesses from the memory the data acquired during the just completed or last data acquisition period. An averaging stage of the microprocessor averages that data to provide averaged data in the form of the average burst duration and the average burst frequency interval. The averaged data is then time stamped by the microprocessor and stored in memory.

As also illustrated in FIG. 1, the monitor 40 includes a serial port 42 in the form of a standard telephone jack which is coupled to a standard telephone wall jack 30 within the patient's home 34 by a telephone cord 32. The monitor 40 further includes a pushbutton switch 44 which, when depressed, activates a modem within the monitor 40 for transmitting by facsimile the averaged data and corresponding time stamps over a standard telephone system 36. The depression of the switch 44 also activates an autodialer within the monitor 40 for automatically dialing the facsimile telephone number of the patient's physician's office 35.

To that end, and in accordance with the present invention, the monitoring system 20 further includes a receiver 31 within the physician's office 35 which includes a facsimile machine 33 and a printer 37. The facsimile machine 33 is coupled to a standard telephone wall jack 39 within the physician's office 35 by a telephone cord 29. As a result, the stored averaged data and the corresponding time stamps may be transmitted from the monitor 40 to a distant facsimile machine 33 to enable the physician to receive the transmitted data and evaluate the patient's condition. Preferably, the facsimile transmission is formatted by the monitor 40 so that the printer 37 may provide a printed display of the received averaged data and time stamps in, for example, a bar graph format to clearly indicate the trend of the electrical activity of the patient's myometrium 16 or uterus 11.

Lastly, the monitor 40 includes a speaker 46 for emitting a discernable audible alarm signal to advise the patient to call the physician. As will be seen hereinafter, whenever the monitor 40 generates a new burst duration and burst frequency interval, it compares this data to a predetermined criteria. If the data exceeds the predetermined criteria, the speaker 46 will sound an alarm to indicate to the patient that the physician should be consulted. The speaker 46 may further be utilized to remind the patient to transmit the averaged data and corresponding time stamps to the physician. To this end, the speaker 46 may be activated by a clock which periodically indicates to the patient when the stored averaged data and corresponding time stamps should be transmitted to the physician's facsimile machine 33.

Figure 2:
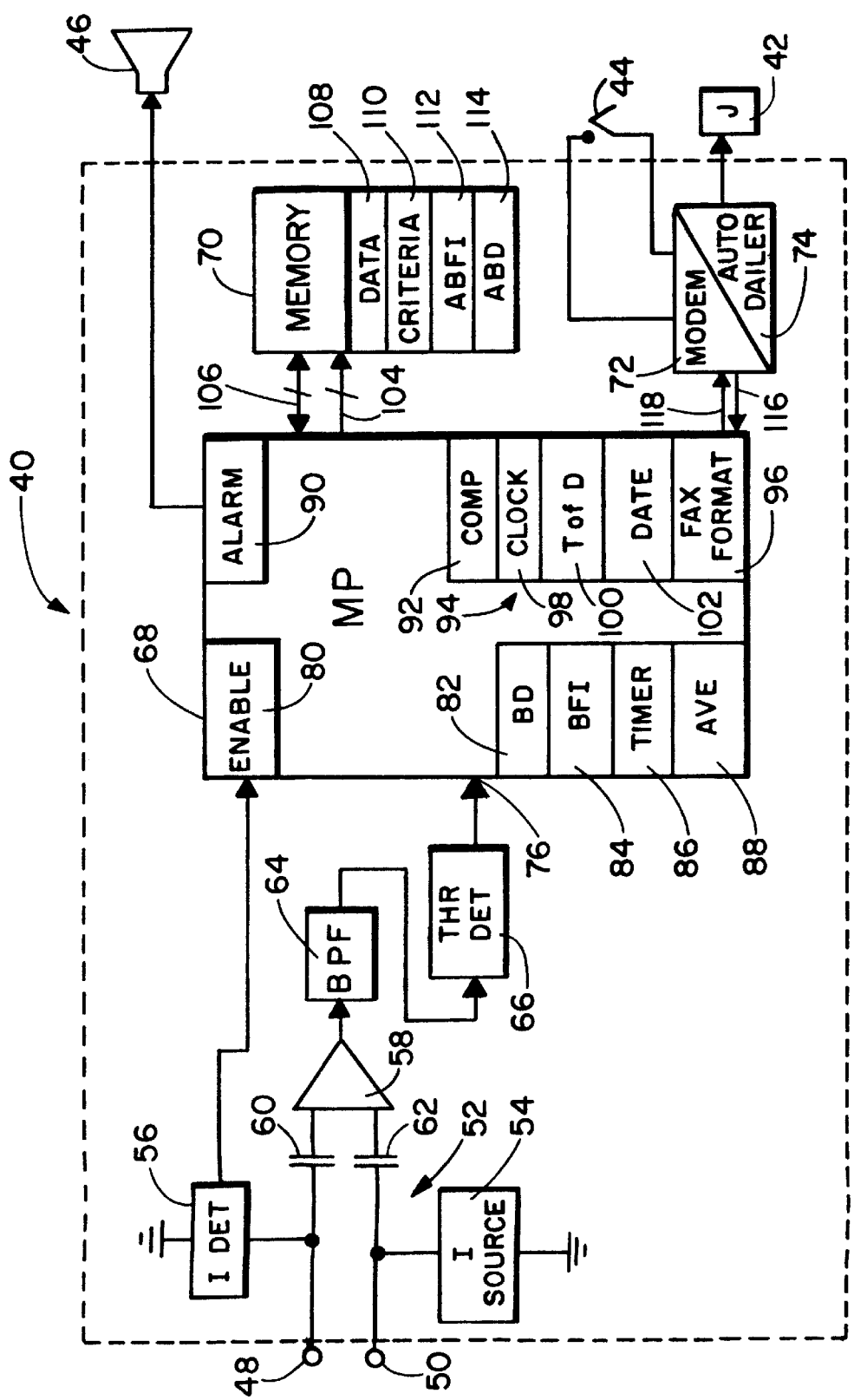
FIG. 2 is a block diagram of a monitor embodying further aspects of the present invention and which may be utilized in the system of FIG. 1.

Referring now to FIG. 2, it illustrates, in block diagram form, the monitor 40 of FIG. 1 in accordance with a preferred embodiment of the present invention. In addition to the standard telephone jack 42, the pushbutton switch 44, and the speaker 46, the monitor 40 includes input terminals 48 and 50, a detector 52 including a current source 54, and a current detector 56, a sense amplifier 58, and capacitors 60 and 62. The monitor further includes a band pass filter 64, a threshold detector 66, a microprocessor 68, a memory 70, a modem 72, and an autodialer 74.

The input terminals 48 and 50 are arranged to receive the connectors 27 and 28 respectively of the leads 26 and 28 respectively as illustrated in FIG. 1. The input terminals 48 and 50 are capacitively coupled to the sense amplifier 58 by the capacitors 60 and 62.

The detector 52 including the current source 54 and current detector 56 detects when the monitor is coupled to the patient. When the input terminals 48 and 50 are coupled to the patient by the electrodes 22 and 24, the patient 10 will present to the input terminals 48 and 50 a load of approximately 1,000 ohms. The current source 54 provides a DC current of about, for example, 1 microamp. When the terminals 48 and 50 of the monitor 40 are coupled to the patient, the current detector 56 will detect a current on the order of 1 microamp. This will indicate to the monitor that the patient is coupled to the monitor. Conversely, when the patient is not coupled to the monitor 40 as by, for example, one of the input terminals 48 or 50 not being coupled to the patient, the current detector 56 will detect no current to indicate to the monitor that the patient is not currently connected to the monitor.

When the patient is coupled to input terminals 48 and 50, the sense amplifier 58 will generate an electromyographic (EMG) signal which is bandpassed filtered by the bandpass filter 64. The bandpass filter 64 preferably has a bandpass from 1 Hertz to 100 Hertz. The bandpass filtered EMG signal is conveyed to the threshold detector 66. The electrical energy bursts of both contractures and contractions of the electromyographic signal are made up of electrical waves having separations of, for example, 300 milliseconds to 900 milliseconds (300 ms to 900 ms). Whenever an electrical wave of the bandpass filtered EMG signal exceeds a threshold magnitude set by the threshold detector 66, the threshold detector will provide an output to an interrupt input 76 of the microprocessor 68.

The implementation of the microprocessor 68 in accordance with this embodiment of the present invention results in a plurality of functional stages. The stages include an enable stage 80, a burst duration stage 82, a burst frequency interval stage 84, a timer 86, and an averaging stage 88. The functional stages further include an alarm stage 90, a comparator stage 92, a clock stage 94, and a facsimile format stage 96. The clock stage 94 includes a clock 98 and a time stamp stage including the time of day stage 100 and a date stage 102.

The microprocessor 68 is arranged to operate in conjunction with the memory 70 which may be coupled to the microprocessor 68 by a multiple-bit address bus 104 and a bi-directional multiple-bit data bus 106. This permits the microprocessor 68 to address desired memory locations within the memory 74 for executing right or read operations. During a right operation, the microprocessor 68 stores data in the memory at memory locations defined by the multiple-bit address bus 104 and conveys the data to the memory over the multiple-bit data bus 106. During a read operation, the microprocessor 68 accesses the memory at stored location identified by the multiple-bit address bus 104 and receives the data from the memory over the bi-directional data bus 106.

The memory 70 includes a plurality of memory locations or portions. These include a data portion 108 for storing data such as burst initiation time stamps, burst completion time stamps, burst durations, and burst frequency intervals. The memory locations or portions of the memory 70 further include a criteria portion 110 for storing alarm criteria, for example, a memory location 112 for storing averaged burst frequency intervals and a further portion 114 for storing averaged burst durations.

As previously mentioned, whenever an electrical wave of the bandpass filtered EMG provided by sense amplifier 58 and bandpass filter 64 exceeds a threshold magnitude established by the threshold detector 66, the threshold detector will provide an output to the interrupt input 76 of the microprocessor 68. The burst duration stage 82 time stamps each interrupt input and stores each time stamp in memory portion 108 of memory 70. It also, with timer 86, starts keeping time from each interrupt input. When the timer 45 has timed a predetermined period of, for example, five seconds without being reset by another interrupt, the burst duration stage 82 considers the current burst to be completed. It then determines the burst duration by accessing the memory 70 at location 108 for the first and last time stamps and computes the time between the first time stamp and the last time stamp as the burst duration. It then stores the burst duration in memory portion 108. The next interrupt will then represent the beginning of the next burst.

Also when a burst is completed, the burst frequency interval stage 84 accesses memory portion 108 of memory 70 for the first time stamp of the just completed burst and the first time stamp of the immediately preceding burst. It then computes the time interval between the first time stamp of the just completed burst and the first time stamp of the immediately preceding burst to determine a burst frequency interval. The burst frequency interval stage 84 then stores the burst frequency interval in memory portion 108 of memory 70.

The foregoing process is carried out for each electrical burst of the myometrium or uterus of the patient. In addition, after each burst is completed, the alarm stage 90 causes the comparator stage 92 to compare the last determined burst duration and burst frequency interval to predetermined criteria. If, for example, the last computed burst duration falls below ninety seconds and the last computed burst frequency interval is less than ten minutes, the alarm 90 responsive to the comparator stage 92 will provide a perceptible indication in the form of an audible alarm from the speaker 46. This alarm may be used to indicate to the patient that the patient's physician should be consulted.

At spaced apart times, as for example, every six hours or four times per twenty-four hour period, the clock 98 of clock stage 94 causes the microprocessor to generate time stamped trended data. To that end, the clock 98 causes the averaging stage 88 to access memory portion 108 of memory 70 for the burst durations and burst frequency intervals determined during the last data acquisition period. The averaging stage 88 averages the burst durations and the burst frequency intervals to provide trended or averaged burst durations and burst frequency intervals. Each average burst duration and burst frequency interval pair is then stored in memory 70 at memory portions 114 and 112 respectively along with a corresponding time stamp indicating when the average burst duration and average burst frequency interval were determined. The time stamps are provided by the time of day stage 100 and date stage 102.

The detector 52 including the current source 54 and current detector 56, as previously mentioned, detects when the monitor 40 is coupled to the patient. When the monitor is coupled to the patient, the enable stage 80 responsive to the current detector 56 enables the microprocessor 68. When the patient is not coupled to the monitor 40, the enable stage 80 disables the microprocessor burst data gathering activity which then makes note of the time in which the monitor 40 is not coupled to the patient. The times at which the monitor 40 are not coupled to the patient are noted by the clock stage 94 so that an inactive time period of the microprocessor 68 due to the patient not being coupled to the monitor will not be mistaken for an unduly long burst frequency interval. As a result, the integrity of the data generated the microprocessor 68 is assured.

As previously mentioned with respect to FIG. 1, occasionally the patient will be called upon to transmit the trended data stored in memory 70 to the physician's office. As illustrated in FIG. 1, the patient connects the telephone jack 42 to the wall jack 30 to connect the monitor to the telephone system. The patient then depresses switch 44 which causes the autodialer 74 to dial the physician's facsimile telephone number. Simultaneously, the microprocessor is initiated over a line 116 to cause the facsimile formatting stage 96 to access the trended data in memory portions 112 and 114 of memory 70, format the data in the form of a facsimile, and convey the data to the modem 72 over a line 118. The facsimile formatting stage 96 preferably formats the facsimile transmission so that once the facsimile is received by the physician's facsimile machine, its printer will print out a bar graph of the average burst durations and average burst frequency intervals along with their corresponding time stamps. This will provide the physician with trending data and a diurnal trend of the patient's uterine electrical activity. The facsimile formatting state 96 may also provide the patient's name or some other form of patient identification.

As can be seen from the foregoing, the present invention provides a monitoring system and method which provides long-term monitoring and trending of uterine activity during the prenatal period of a human. The data generated by the monitor and provided to the physician provides assistance in diagnosing potential prenatal complications and most notably, premature labor.

While a particular embodiment of the present invention has been shown and described, modifications may be made, and it is therefore intended to cover in the appended claims all such changes and modifications which fall within the true spirit and scope of the invention.

What is claimed is:

1. A system for monitoring a prenatal condition of a patient and reporting the monitored condition, the system comprising:
   a monitor adapted to be coupled to the patient including means for generating an electrical signal representing uterine electrical activity of the patient, analyzing means for analyzing a characteristic of the electrical signal to generate data indicative of the condition, and a transmitter for transmitting the generated data; and
   a receiver, separated from the monitor for receiving the transmitted data and including a display for displaying the received data.

2. A system as defined in claim 1 wherein the monitor includes a detector for detecting when the monitor is coupled to the patient.

3. A system as defined in claim 1 wherein the monitor includes a comparator for comparing the generated data to predetermined criteria and an alarm responsive to the comparator for providing a perceptible indication when the generated data satisfies the predetermined criteria.

4. A system as defined in claim 1 wherein the transmitter includes a modem.

5. A system as defined in claim 1 wherein the transmitter includes means for generating a facsimile.

6. A system as defined in claim 5 wherein the receiver includes means for receiving the facsimile.

7. A system as defined in claim 1 wherein the receiver includes a printer for displaying the received data in printed form.

8. A system as defined in claim 1 wherein the transmitter includes an auto dialer.

9. A system as defined in claim 1 wherein the monitor includes a memory for storing the generated data.

10. A system as defined in claim 1 wherein the monitor further includes a clock for time stamping a portion of the generated data to provide time stamped data.

11. A system as defined in claim 10 wherein the monitor further includes a memory for storing the time stamped data and wherein the transmitter transmits the time stamped data.

12. A system as defined in claim 1 wherein the analyzing means includes trending means for providing trended data to the transmitter.

13. A system as defined in claim 12 wherein the monitor includes a clock and wherein the trending means is responsive to the clock for generating the trended data at spaced apart times.

14. A system as defined in claim 13 wherein the clock includes means for time stamping the trended data.

15. A system as defined in claim 12 further including a memory for receiving the trended data from the analyzing means and conveying the trended data to the transmitter.

16. A monitor for monitoring a prenatal condition of a patient and reporting the monitored condition, the monitor comprising:
    electrical signal means for generating an electrical signal representing uterine electrical activity of the patient;
    analyzing means for analyzing a characteristic of the electrical signal to generate data indicative of the condition; and
    a transmitter for transmiting the generated data.

17. A monitor as defined in claim 16 further including means for coupling the electrical signal generating means to the patient and a detector for detecting when the electrical signal generating means is coupled to the patient.

18. A monitor as defined in claim 16 further including a comparator for comparing the generated data to predetermined criteria and an alarm responsive to the comparator for providing a perceptible indication when the generated data satisfies the predetermined criteria.

19. A monitor as defined in claim 16 wherein the transmitter includes a modem.

20. A monitor as defined in claim 16 wherein the transmitter includes means for generating a facsimile.

21. A monitor as defined in claim 16 wherein the transmitter includes an auto dialer.

22. A monitor as defined in claim 16 further including a memory for storing the generated data.

23. A monitor as defined in claim 16 further including a clock for time stamping a portion of the generated data to provide time stamped data.

24. A monitor as defined in claim 23 further including a memory for storing the time stamped data and wherein the transmitter transmits the time stamped data.

25. A monitor as defined in claim 16 wherein the analyzing means includes trending means for providing trended data to the transmitter.

26. A monitor as defined in claim 25 further including a clock and wherein the trending means is responsive to the clock for generating the trended data at spaced apart times.

27. A monitor as defined in claim 26 wherein the clock includes means for time stamping the trended data.

28. A monitor as defined in claim 25 further including a memory for receiving the trended data from the analyzing means and conveying the trended data to the transmitter.

* * * * *